(12) United States Patent
Thomas et al.

(10) Patent No.: US 9,134,251 B2
(45) Date of Patent: Sep. 15, 2015

(54) POROUS CHEMICAL INDICATOR FOR GASEOUS MEDIA

(75) Inventors: J. Christopher Thomas, St. Paul, MN (US); Neal A. Rakow, Woodbury, MN (US); Duane D. Fansler, Dresser, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 13/816,510

(22) PCT Filed: Sep. 15, 2011

(86) PCT No.: PCT/US2011/051767
§ 371 (c)(1),
(2), (4) Date: Apr. 10, 2013

(87) PCT Pub. No.: WO2012/040032
PCT Pub. Date: Mar. 29, 2012

(65) Prior Publication Data
US 2013/0189166 A1    Jul. 25, 2013

Related U.S. Application Data

(60) Provisional application No. 61/385,589, filed on Sep. 23, 2010.

(51) Int. Cl.
*G01N 21/75* (2006.01)
*G01N 21/78* (2006.01)
*G01N 31/22* (2006.01)
(Continued)

(52) U.S. Cl.
CPC .............. *G01N 21/783* (2013.01); *G01N 31/22* (2013.01); *G01N 31/221* (2013.01); *A61B 10/0045* (2013.01); *A61B 17/083* (2013.01); *A61B 17/085* (2013.01); *B01L 2200/16* (2013.01); *B01L 2300/044* (2013.01); *B01L 2300/046* (2013.01); *G01N 21/78* (2013.01); *G01N 2001/028* (2013.01); *G01N 2021/773* (2013.01); *G01N 2021/7796* (2013.01); *G01N 2035/00108* (2013.01); *G01N 2035/00148* (2013.01); *Y10T 156/10* (2015.01)

(58) Field of Classification Search
CPC .......... B01L 2200/16; B01L 2300/044; B01L 2300/046; G01N 2001/028; G01N 2035/00108; G01N 2035/00148; G01N 21/78; A61B 10/0045; A61B 17/083; A61B 17/085
USPC .................................... 422/83, 84, 85, 86, 87
See application file for complete search history.

(56) References Cited

U.S. PATENT DOCUMENTS

| 1,537,519 | A | 12/1924 | Yablick |
| 3,966,440 | A | 6/1976 | Roberts |

(Continued)

FOREIGN PATENT DOCUMENTS

| EP | 0263692 | 4/1988 |
| EP | 0901009 | 3/1999 |

(Continued)

*Primary Examiner* — Dennis M White
(74) *Attorney, Agent, or Firm* — Jeffrey M. Olofson (57) ABSTRACT

Chemical indicators for acidic or basic gases include an inert, porous substrate, an indicator dye or mixture of dyes contained within at least some of the pores of the inert, porous substrate, and an inert adhesive layer attached to the inert, porous substrate. The porous substrate may be a microporous substrate.

20 Claims, 1 Drawing Sheet

(51) Int. Cl.
  *A61B 17/08* (2006.01)
  *A61B 10/00* (2006.01)
  *G01N 35/00* (2006.01)
  *G01N 1/02* (2006.01)
  *G01N 21/77* (2006.01)

(56) References Cited

U.S. PATENT DOCUMENTS

| | | |
|---|---|---|
| 4,146,887 A | 3/1979 | Magnante |
| 4,154,586 A | 5/1979 | Jones |
| 4,155,358 A | 5/1979 | McAllister |
| 4,326,514 A | 4/1982 | Eian |
| 4,421,719 A | 12/1983 | Burleigh |
| 4,530,706 A | 7/1985 | Jones |
| 4,539,256 A | 9/1985 | Shipman |
| 4,597,942 A | 7/1986 | Meathrel |
| 4,684,380 A | 8/1987 | Leichnitz |
| 4,777,073 A | 10/1988 | Sheth |
| 4,847,594 A | 7/1989 | Stetter |
| 4,994,117 A * | 2/1991 | Fehder .......................... 436/133 |
| 5,120,594 A | 6/1992 | Mrozinski |
| 5,169,727 A | 12/1992 | Boardman |
| 5,209,971 A | 5/1993 | Babu |
| 5,238,623 A | 8/1993 | Mrozinski |
| 5,297,544 A | 3/1994 | May |
| 5,323,774 A | 6/1994 | Fehlauer |
| 5,376,554 A | 12/1994 | Vo-Dinh |
| 5,512,882 A | 4/1996 | Stetter |
| 5,659,296 A | 8/1997 | Debe |
| 5,666,949 A | 9/1997 | Debe |
| 5,695,640 A * | 12/1997 | Tseng ...................... 210/500.38 |
| 5,853,669 A | 12/1998 | Wolfbeis |
| 6,264,864 B1 | 7/2001 | Mackay |
| 6,348,258 B1 | 2/2002 | Topolkaraev |
| 6,375,725 B1 | 4/2002 | Bernard |
| 6,497,756 B1 | 12/2002 | Curado |
| 6,533,119 B1 | 3/2003 | Hansen |
| 6,701,864 B2 | 3/2004 | Watson, Jr. |
| 7,442,237 B1 | 10/2008 | Gardner |
| 2004/0135684 A1 | 7/2004 | Steinthal |
| 2004/0142495 A1 | 7/2004 | Hartman |
| 2004/0189982 A1 | 9/2004 | Galarneau |
| 2004/0223876 A1 | 11/2004 | Kirollos |
| 2005/0042136 A1 | 2/2005 | Marganski |
| 2005/0188749 A1 | 9/2005 | Custer |
| 2006/0094320 A1 | 5/2006 | Chen |
| 2009/0035179 A1 | 2/2009 | Rakow |
| 2010/0022010 A1 | 1/2010 | Stevens |

FOREIGN PATENT DOCUMENTS

| | | |
|---|---|---|
| WO | WO 2004/057314 | 7/2004 |
| WO | WO 2004/059281 | 7/2004 |
| WO | WO 2006/032719 | 3/2006 |

* cited by examiner

POROUS CHEMICAL INDICATOR FOR GASEOUS MEDIA

FIELD OF THE DISCLOSURE

The present disclosure pertains to chemical indicators for acidic or basic gases, devices incorporating such indicators and methods of preparing chemical indicators for acidic or basic gases.

BACKGROUND

A variety of techniques are used to detect the presence of acids, acidic substances, bases and basic substances in liquids. For example, electronic devices such as pH meters can be used or chemical detection techniques such as Litmus paper can be used.

The detection of the presence of acids or bases in gases is more difficult and is becoming increasingly important. In a variety of work and other environments, acidic or basic gases may be present, and their presence can provide a hazard to those exposed to these gases. Techniques suitable for the detection of acids or bases in liquids typically are not suitable for the detection of acids or bases in gaseous media.

SUMMARY

The present disclosure comprises chemical indicators for acidic or basic gases. The chemical indicators comprise an inert, porous substrate, an indicator dye or mixture of dyes contained within at least some of the pores of the inert, porous substrate, and an inert adhesive layer attached to the inert, porous substrate. In some embodiments, the porous substrate comprises a microporous substrate.

Also disclosed are devices incorporating chemical indicators for acidic or basic gases. The devices comprise a case, and at least one chemical indicator within the case. The chemical indicator comprises an inert, porous substrate, and an indicator dye or mixture of dyes contained within at least some of the pores of the inert, porous substrate, and an inert adhesive layer attached to the inert, porous substrate. The porous substrate may comprise a microporous substrate. In some embodiments, the case comprises a respirator cartridge.

Further, methods of preparing chemical indicators for acidic or basic gases are disclosed. The methods of preparing a chemical indicator comprise providing an inert, porous substrate, providing an indicator dye solution, and applying the indicator dye mixture to the inert, porous substrate such that at least some of the indicator dye mixture enters the pores of the inert, porous substrate. A layer of inert adhesive is applied to the inert, porous substrate. In some embodiments, the adhesive layer is applied by laminating an inert adhesive layer to the porous substrate.

BRIEF DESCRIPTION OF THE DRAWINGS

The disclosure may be more completely understood in consideration of the following detailed description of various embodiments of the disclosure in connection with the accompanying drawings.

In the following description of the illustrated embodiments, reference is made to the accompanying drawings, in which is shown by way of illustration, various embodiments in which the disclosure may be practiced. It is to be understood that the embodiments may be utilized and structural changes may be made without departing from the scope of the present disclosure. The figures are not necessarily to scale. Like numbers used in the figures refer to like components. However, it will be understood that the use of a number to refer to a component in a given figure is not intended to limit the component in another figure labeled with the same number.

DETAILED DESCRIPTION

A variety of environments, including work environments, may contain acidic or basic gases that may be harmful to workers present. A variety of protective clothing and devices have been developed to protect against exposure to these acidic or basic gases. In particular, respirators have been developed to protect the respiratory system from damage by acidic or basic gases. Such respirators often contain filter cartridges with materials to absorb or otherwise neutralize the acidic or basic gases. When such respirators are used, it is generally desirable to have a method to determine an end of service life, i.e. the point at which the respirator no longer provides protection from acidic or basic gases. Frequently End of Service Life Indicators (ESLI) are used. Such indicators provide a visual, electronic or other cue that the respirator or filter cartridge within a respirator is approaching the end of its useful life and should be replaced.

In this disclosure are presented porous chemical indicators that can be used, among other uses, as ESLI for acidic or basic gas respirator devices. The chemical indicators comprise an inert, porous substrate, an indicator dye or mixture of dyes contained within at least some of the pores of the inert, porous substrate, and an inert adhesive layer attached to the porous substrate. In some embodiments the porous substrate comprises a microporous substrate. Examples of microporous substrates include films and membranes. Microporous films and membranes have a structure that enables fluids to flow through them. The effective pore size is at least several times the mean free path of the flowing molecules, namely from several micrometers down to about 100 Angstroms. Typically a microporous substrate is one in which substantially all of the pores have a diameter of less than 1,000 micrometers. More typically microporous substrates have pore diameters of from 1 to about 500 micrometers, or 1 to about 100 micrometers or even 1 to about 10 micrometers.

As used herein, the term "indicator" refers to a device, layer or series of layers that upon exposure to an analyte, such as an acid, undergoes a detectable change. Typically the detectable change is a visual change. When the visual change is a change in color, the indicator is said to be "colorimetric".

As used herein, the term "acid gases or acidic gases" refers to gases that contain some acidic component. The acidic component may itself be a gas, such as, for example hydrogen chloride gas, but the acidic component need not itself be a gas, but may merely be present in the gas or gas mixture. Additionally, acidic gases may not themselves be acids but acids may result from combination with other materials present in the atmosphere.

As used herein, the term "base gases or basic gases" refers to gases that contain some basic component. The basic component may itself be a gas, such as, for example ammonia, but the basic component need not itself be a gas, but may merely be present in the gas or gas mixture. Additionally, basic gases may not themselves be bases but bases may result from combination with other materials present in the atmosphere.

As used herein, the term "inert" when used to describe porous substrates or adhesive layers, means that the porous substrates or adhesive layers are substantially unreactive with acidic or basic gases and remain substantially physically and chemically unchanged when exposed to acidic or basic gases. Typically, inert layers are prepared from materials that are themselves substantially free of acidic or basic components.

Disclosed herein are chemical indicators that comprise an inert, porous substrate, an indicator dye or dye mixture contained within at least some of the pores of the inert, porous substrate, and an inert adhesive layer attached to the inert, porous substrate. The chemical indicators of this disclosure are suitable for detecting acidic or basic gases present within a gaseous media.

The chemical indicators of this disclosure comprise an inert, porous substrate. The inert, porous substrate serves as a container for the indicator dye or dye mixture. Additionally, the inert, porous substrate acts as a diffusion layer, facilitating transport of the acidic gas or basic gas to the indicator dye or dye mixture. In some embodiments, the inert porous substrate may be opaque. Many porous and microporous substrates are opaque, even if prepared from optically transparent materials, because the surfaces and internal structure of these substrates scatter visible light. In the present disclosure, this opacity may be advantageous as it can provide a background for monitoring changes in the indicator dye or dye mixture, such as, for example, color changes.

A variety of materials can be used to prepare the inert, porous substrate. Either inorganic or organic materials may be used. In some embodiments, hydrocarbon-based polymeric materials are used. Polyolefinic materials, such as, for example, polyethylene, polypropylene, and the like and blends thereof are a particularly useful class of materials for preparing the inert, porous substrate.

In some embodiments, the inert, porous substrate comprises a microporous membrane. Suitable microporous membranes for use as the inert, porous substrate include those resulting from a phase inversion method in which an initially homogeneous polymer solution is cast and exposed to a cooler interface (e.g., a water bath or chilled casting wheel), and phase separation is induced in the solution film by lowering the temperature (thermally induced phase separation or "TIPS"). Suitable TIPS films or membranes may possess a broad range of physical film properties and microscopic pore sizes. They may be relatively rigid or non-rigid substrates prepared from any of a variety of polymers. TIPS membranes made according to the teachings of U.S. Pat. Nos. 4,539,256 and 5,120,594 are suitable for use in this disclosure and may comprise high density polyethylene (HDPE), polypropylene, polyvinylidenefluoride (PVDF), polyethylene-vinyl alcohol copolymer (e.g., available under the trade designation EVAL F101A from EVAL Company of America (EVALCA), Houston, Tex.), for example. The membrane may comprise a combination of materials such as a TIPS HDPE or a polypropylene membrane coated with a hydrophilic polymer (e.g., polyethylene-vinyl alcohol copolymer or EVAL).

Other useful materials suitable for use as the inert, porous substrate include: non-rigid polymers and other materials including nylon materials such as positively charged Nylon 6,6 materials (e.g., those available under the trade designation Biodyne B from Pall Corporation, Pensacola, Fla. and those available under the trade designation Magnaprobe from GE Osmonics Labstore in Minnetonka, Minn.); a hydrophilic treated polypropylene membrane with 0.45 micrometer pore size, available under the trade designation GHP-450 from Pall Corporation; polyolefins (with a hydrophilic treatment); polyester; nitrocellulose; cellulose acetate; hydrophilic poly tetrafluoroethylene (PTFE); polycarbonate; and the like. Additional useful materials include nonwoven, melt blown, or spunbond webs made from, for example, polyolefins, nylon, polyvinylidene fluoride (PVDF), and the like, prepared with small effective fiber diameter. Also suitable are melt blown and spunbond webs that are compressed with pressure to reduce substrate thickness and pore size as described in U.S. Pat. No. 6,533,119. Additional substrate materials include, particle-filled microporous substrates are described in U.S. Pat. Nos. 6,264,864, 6,348,258, 4,777,073 and porous substrates prepared from nanosized electrospun fibers as described in US Patent Publication 2006/094320. Combinations of materials may be used in the inert, porous substrate and the foregoing description is to be understood to include the aforementioned materials alone and in combination with other materials.

The chemical indicators of this disclosure also comprise an indicator dye or dye mixture. The indicator dye or dye mixture produces a detectable change, typically a color change, upon exposure to a target analyte. In some embodiments the target analyte is an acidic gas, in other embodiments the target analyte is a basic gas.

A wide variety of materials may be used in the chemical indicators of this disclosure as the indicator dye or dye mixture. Upon exposure to an analyte, the indicator dye or dye mixture undergoes a detectable change. Typically the detectable change is a colorimetric change and is detectable with the naked eye. This detectable change can take a variety of modes, such as, for example, from a colored state to a colorless or less colored state, from a colorless state to a colored state, or from one color to different color.

Many indicator dyes can be used to detect either acidic or basic gases. Generally, the indicator dye or dye mixture is in a form such that a detectable change occurs upon exposure to the desired analyte. For example, if it is desired that the indicator dye detect the presence of an acidic gas, the indicator dye typically is in a basic form. Similarly, if it is desired that the indicator dye detect the presence of a basic gas, the indicator dye typically is in an acidic form.

If the chemical indicator is designed to detect acidic gases, an indicator dye or dye mixture is selected that upon exposure to acidic species undergoes a detectable change, such as for example, a color change. A wide range of such indicator dyes are available. Various forms of indicator dyes or dye mixtures may be useful, including, for example acidic or basic forms, and various salts that provide for improved solubility or reactivity characteristics. Suitable dyes may be located, for example, in "The Sigma-Aldrich Handbook of Stains, Dyes, and Indicators", Floyd J. Green, 1990, The Sigma-Aldrich Chemical Company, Inc. Examples of suitable dyes for detecting acidic gases include, for example, Bromothymol Blue, Methyl Red and Phenol Red, Bromocresol Purple, Bromocresol Green, Phenophthalein, and Congo Red when used in their basic forms. Of these, Bromothymol Blue, Methyl Red and Phenol Red, are particularly suitable.

If the chemical indicator is designed to detect basic gases, an indicator dye or dye mixture is selected that upon exposure to basic species undergoes a detectable change, such as, for example, a color change. A wide range of such indicator dyes are available. Examples of suitable dyes for detecting basic gases include, for example, the same indicators described above where the dyes are present in their acidic forms.

The chemical indicators of this disclosure comprise an inert adhesive layer attached to the inert, porous substrate. The inert adhesive layer can serve to adhere a substrate or film to the porous substrate or can serve as a mounting surface, permitting the chemical indicator to be mounted directly to a variety of surfaces. The inert adhesive layer is selected such that it does not interact substantially with the indicator dye or mixture of indicator dyes. Typically, the adhesive layer is substantially free of acidic or basic moieties that can interact with or even react with the indicator dye or dyes. Also, it is desirable that the adhesive layer not solubilize the indicator dye or mixture of dyes.

A wide variety of adhesives are useful in the inert adhesive layer of the chemical indicators of this disclosure. Typically the adhesive is a pressure sensitive adhesive. Pressure sensitive adhesive compositions are well known to those of ordinary skill in the art to possess properties including the following: (1) aggressive and permanent tack, (2) adherence with no more than finger pressure, (3) sufficient ability to hold onto an adherend, and (4) sufficient cohesive strength to be cleanly removable from the adherend. Materials that have been found to function well as pressure sensitive adhesives are polymers designed and formulated to exhibit the requisite viscoelastic properties resulting in a desired balance of tack, peel adhesion, and shear holding power. Obtaining the proper balance of properties is not a simple process.

Useful pressure sensitive adhesives include those based on natural rubbers, synthetic rubbers, styrene block copolymers, acrylics, poly-α-olefins, or silicones.

Useful natural rubber pressure sensitive adhesives generally contain masticated natural rubber, from 25 parts to 300 parts of one or more tackifying resins to 100 parts of natural rubber, and typically from 0.5 to 2.0 parts of one or more antioxidants. Natural rubber may range in grade from a light pale crepe grade to a darker ribbed smoked sheet and includes such examples as CV-60, a controlled viscosity rubber grade and SMR-5, a ribbed smoked sheet rubber grade.

Another useful class of pressure sensitive adhesives are those comprising synthetic rubber. Such adhesives are generally rubbery elastomers, which are either self-tacky or non tacky and require tackifiers. Self-tacky synthetic rubber pressure sensitive adhesives include for example, butyl rubber, a copolymer of isobutylene with less than 3 percent isoprene, polyisobutylene, a homopolymer of isoprene, polybutadiene, such as "TAKTENE 220 BAYER" or styrene/butadiene rubber. Butyl rubber pressure sensitive adhesives often contain an antioxidant such as zinc dibutyl dithiocarbamate. Polyisobutylene pressure sensitive adhesives do not usually contain antioxidants. Synthetic rubber pressure sensitive adhesives, which generally require tackifiers, are also generally easier to melt process. They comprise polybutadiene or styrene/butadiene rubber, from 10 parts to 200 parts of a tackifier, and generally from 0.5 to 2.0 parts per 100 parts rubber of an antioxidant. An example of a synthetic rubber is "AMERIPOL 1011A", a styrene/butadiene rubber available from BF Goodrich.

Styrene block copolymer pressure sensitive adhesives generally comprise elastomers of the A-B or A-B-A type, where A represents a thermoplastic polystyrene block and B represents a rubbery block of polyisoprene, polybutadiene, or poly (ethylene/butylene), and resins. Examples of the various block copolymers useful in block copolymer pressure sensitive adhesives include linear, radial, star and tapered styrene-isoprene block copolymers such as "KRATON D1107P", available from Shell Chemical Co., and "EUROPRENE SOL TE 9110", available from EniChem Elastomers Americas, Inc.; linear styrene-(ethylene-butylene) block copolymers such as "KRATON G1657", available from Shell Chemical Co.; linear styrene-(ethylene-propylene) block copolymers such as "KRATON G1750X", available from Shell Chemical Co.; and linear, radial, and star styrene-butadiene block copolymers such as "KRATON D1118X", available from Shell Chemical Co., and "EUROPRENE SOL TE 6205", available from EniChem Elastomers Americas, Inc. The polystyrene blocks tend to form domains in the shape of spheroids, cylinders, or plates that causes the block copolymer pressure sensitive adhesives to have two phase structures. Resins that associate with the rubber phase generally develop tack in the pressure sensitive adhesive. Resins that associate with the thermoplastic phase tend to stiffen the pressure sensitive adhesive.

Acrylic pressure sensitive adhesives generally have a glass transition temperature of about −20° C. or less and may comprise from 100 to 80 weight percent of a $C_3$-$C_{12}$ alkyl ester component such as, for example, isooctyl acrylate, 2-ethyl-hexyl acrylate, lauryl acrylate, and n-butyl acrylate and from 0 to 20 weight percent of a reinforcing component such as, for example, ethylene vinyl acetate, or styrene macromer. The acrylic pressure sensitive adhesives may be self-tacky or tackified.

Poly-α-olefin pressure sensitive adhesives, also called poly (1-alkene) pressure sensitive adhesives, generally comprise either a substantially uncrosslinked polymer or a uncrosslinked polymer that may have radiation activatable functional groups grafted thereon as described, for example, in U.S. Pat. No. 5,209,971 (Babu, et al). The poly-α-olefin polymer may be self tacky and/or include one or more tackifying materials. Useful poly-α-olefin polymers include, for example, $C_3$-$C_{18}$ poly(1-alkene) polymers, preferably $C_5$-$C_{12}$ α-olefins and copolymers of those with $C_3$ and more preferably $C_6$-$C_8$ and copolymers of those with $C_3$.

Suitable silicone pressure sensitive adhesives are formed from mixtures of compounds in which are present vinylic groups and hydrosilane groups. Vinylic groups comprise terminal carbon-carbon double bonds and hydrosilane groups comprise at least one terminal Si—H bond. Typically, elastomeric polymers are formed through the hydrosilylation reaction shown below:

A-CH=CH$_2$+B—Si—H→A-CH$_2$—
<br>CH$_2$—Si—B          Hydrosilylation reaction Typically, a catalyst, such as a noble metal catalyst such as a platinum, palladium, rhodium or iridium catalyst, is used to catalyze the hydrosilylation reaction. The compound containing the vinylic group may be a silicone, the compound containing the hydrosilane may be a silicone or both may be silicones. As used herein, the terms "silicone" and "siloxane" are used interchangeably and refer to units with dialkyl or diaryl siloxane (—SiR$_2$O—) repeat units. Examples of silicone pressure sensitive adhesives prepared by hydrosilylation are described, for example, in U.S. Pat. No. 5,169,727 (Boardman).

In some embodiments, it may be desirable that the adhesive layer be optically transparent or optically clear. Unless otherwise indicated, "optically transparent" refers to an article, film or adhesive that has a high light transmittance over at least a portion of the visible light spectrum (about 400 to about 700 nm). Unless otherwise indicated, "optically clear" refers to an article, film or adhesive that has a high light transmittance over at least a portion of the visible light spectrum (about 400 to about 700 nm), and that exhibits low haze. Optical transparency can permit the chemical indicator to be monitored from the adhesive side as well as from the inert, porous substrate side.

In some embodiments, the adhesive layer may be a transfer tape. The term "transfer tape" as used herein refers to a double sided adhesive tape that has adhesive on both exposed surfaces. In some transfer tapes, the exposed surfaces are simply the two surfaces of a single adhesive layer. Other transfer tapes are multilayer transfer tapes with at least two adhesive layers that may be the same or different, and in some instances intervening layers that mayor may not be adhesive layers. For example, a multi-layer transfer tape may be a 3 layer construction with an adhesive layer, a film layer and another adhesive layer. The film layer can provide handling and/or tear strength or other desirable properties. Typically, transfer tapes are provided on a release substrate, such as a release liner, to aid handling and delivery of the transfer tape.

A variety of optional additional layers may be present in the chemical indicators of this disclosure. In some embodiments, for example, it may be desirable to include a non-porous substrate layer to the adhesive layer of the chemical indicator. This non-porous substrate layer may be a film or sheet or it may be a more rigid substrate such as glass or ceramic. In some embodiments, the non-porous substrate may be removable, such as a release liner. In other embodiments, the film or sheet may be tinted or colored in order to help provide a color contrast for the indicator dye. For example, it may be desirable, in some embodiments, to have a white film attached to the adhesive layer so that a color change in the indicator dye, such as from white to red or pink, is more noticeable. In this way an observer, when monitoring the chemical indicator, could look through the inert, porous substrate to the adhesive layer covered with a film layer and better see the colorimetric change of the indicator dye. Additionally, the film or sheet may be transparent to allow an observed to monitor the chemical indicator by looking through the film and adhesive layers. The film or sheet may be prepared from any suitable material, for example metal foils or polymeric materials such as polyethylene, polypropylene, other polyolefinic polymers, polyesters and the like. In some embodiments, the film or sheet is a tape backing, and the adhesive layer and the film together form a tape that can be laminated to the inert, porous substrate to form the chemical indicator.

In some embodiments in which a film is included in the chemical indicator construction, it may be desirable to have indicia printed on the film, either before or after the film is incorporated into the chemical indicator. For example, square, rectangular or other shaped figures may be printed on the film to indicate an area for the observer to look to observe the color change of the indicator. In other embodiments, a reference color strip or layer may be printed on the film to mimic either the initial or activated state of the indicator. For example, if the indicator changes to a red color upon activation, a red strip may be printed on the film layer with accompanying text stating for example, "When the indicator is this color, acid gases are present". The indicia may also be a text message with information or instructions for the observer, such as, for example, "Check this indicator strip before opening door to storage room".

In some embodiments, it may be desirable to have a second adhesive layer. This second adhesive layer is present on at least a portion of the exterior surface of the non-porous substrate. The exterior surface is the one opposite to the surface that is attached to the inert adhesive layer of the chemical indicator. This adhesive layer can be used, for example, to attach the chemical indicator to a surface. This second adhesive layer can comprise the same adhesive material as the inert adhesive layer, or it may comprise a different adhesive material. This adhesive layer may be continuous or discontinuous and may contain a microstructured surface. The second adhesive layer can be covered with a release liner to protect the adhesive surface prior to attachment to a surface. This release liner can contain a microstructured surface which can generate a microstructured topography onto the surface of the second adhesive layer when the release liner is removed. Such surface structuring of adhesives can be beneficial to aid air egress when the adhesive layer is applied to a surface to form an adhesive bond.

Figure 1:
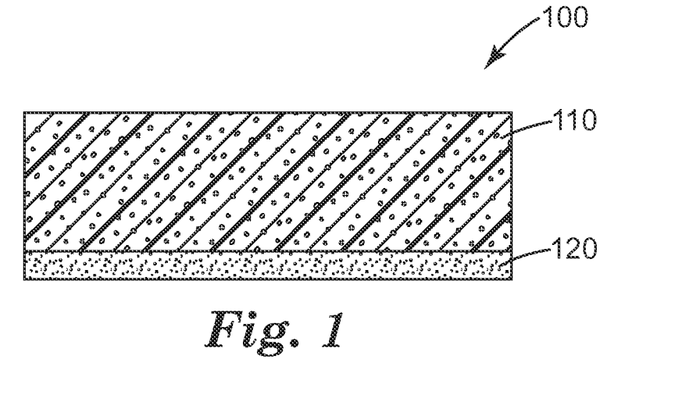
FIG. 1 shows a cross sectional view of a porous chemical indicator of this disclosure.

Referring to the figures, FIG. 1 shows a cross sectional view of a porous chemical indicator of this disclosure. Porous chemical indicator 100 comprises inert porous substrate 110 which contains indicator dye or dyes (not shown) and inert adhesive layer 120.

Figure 2:
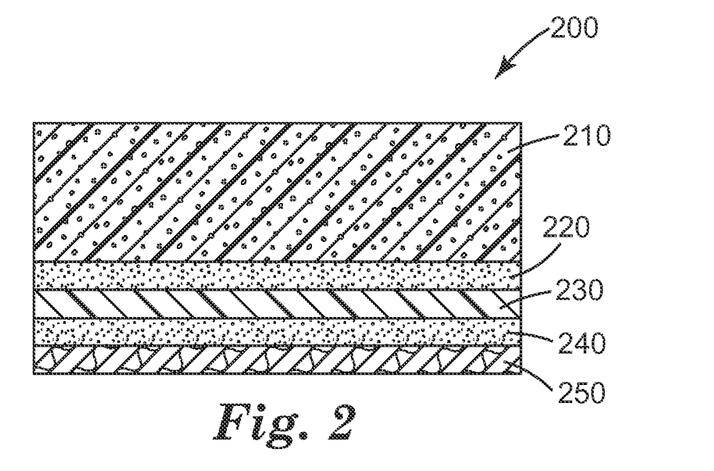
FIG. 2 shows a cross sectional view of an alternative porous chemical indicator of this disclosure.

FIG. 2 shows a cross sectional view of an alternative embodiment of a porous chemical indicator of this disclosure. Porous chemical indicator 200 comprises inert porous substrate 210 which contains indicator dye or dyes (not shown) inert adhesive layer 220, film layer 230, and optional adhesive layer 240 and optional release liner 250. As described above, adhesive layers 220 and 240 may be the same or different. In some embodiments, adhesive layers 220 and 240 are both optically clear adhesive layers. Film layer 230 may be optically transparent. Adhesive layer 220 and film layer 230 together may comprise a tape article that has been laminated to porous substrate 210.

The chemical indicators of this disclosure can be used to form a variety of different devices and articles. Additionally, the indicators can be incorporated into existing devices and articles to provide an indicating function to those devices and articles.

Among the useful devices which can be prepared using the indicators of this disclosure are ESLI, or End of Service Life Indicators. As mentioned above, ESLI are useful with devices such as air purifying respirators, to provide an indication of end of the useful service life of the respirator. In some cases, regulations, such as government regulations, require that an ESLI device be employed where respirators are used unless a change out schedule is used. Patent references that refer to ESLIs in particular include U.S. Pat. No. 1,537,519 (Yablick), U.S. Pat. No. 3,966,440 (Roberts), U.S. Pat. No. 4,146,887 (Magnante), U.S. Pat. No. 4,154,586 (Jones et al), U.S. Pat. No. 4,155,358 (McAllister et al.), U.S. Pat. No. 4,326,514 (Eian), U.S. Pat. No. 4,421,719 (Burleigh), U.S. Pat. No. 4,530,706 (Jones), U.S. Pat. No. 4,597,942 (Meathrel), U.S. Pat. No. 4,684,380 (Leichnitz), U.S. Pat. No. 4,847,594 (Stetter), U.S. Pat. No. 5,297,544 (May et al.), U.S. Pat. No. 5,323,774 (Fehlauer), U.S. Pat. No. 5,376,554 (Vo-Dinh), U.S. Pat. No. 5,512,882 (Stetter et al.), U.S. Pat. No. 5,666, 949 (Debe et al. '949), U.S. Pat. No. 5,659,296 (Debe et al. '296), U.S. Pat. No. 6,375,725 B1 (Bernard et al.), U.S. Pat. No. 6,497,756 B1 (Curado et al.) and U.S. Pat. No. 6,701,864 B2 (Watson, Jr. et al.); US. Patent Application Publication Nos. US 2004/0135684 A1 (Steinthal et al.), US 2004/0189982 A1 (Galarneau et al.), US 2004/0223876 A1 (Kirollos et al.) and US 2005/0188749 A1 (Custer et al.); and PCT Published Patent Application No. WO 2004/057314 A2.

Additionally, the chemical indicators of this disclosure can be used as passive monitors to provide a warning of acidic gas or basic gas release. For example, the chemical indicators can be mounted on a wall outside of a storage facility, processing facility and the like to provide a warning by a detectable change upon exposure to acidic or basic gases. For example, the chemical indicator could be adhered to the window of a door at the entrance to a storage facility where acidic or basic gases are stored. A worker could check the chemical indicator before opening the door to determine if there has been an accidental release of acidic or basic gases.

A variety of methods can be used to prepare the chemical indicators of this disclosure. For example, an inert, porous substrate can be provided. This inert, porous substrate can be purchased or prepared by the methods described above. In some embodiments the inert, porous substrate is a polypropylene TIPS membrane as described above. This inert, porous substrate can be coated with a solution of an indicator dye, or mixture of dyes, dissolved in a solvent. Any suitable solvent can be used, particularly suitable ones include: alcohols such as methanol, ethanol, isopropanol and the like; ketones such as acetone and methyl ethyl ketone; esters such as ethyl acetate; ethers such as ethyl ether and tetrahydrofuran; and halocarbons such as dichloromethane. Suitable dyes to prepare acid gas indicators include, for example, Bromothymol Blue, Methyl Red, and Phenol Red. In some embodiments, the indicator dye is dissolved in ethanol. An aqueous base, such as sodium hydroxide or potassium hydroxide, can be added to make the formed indicator solution basic.

The dye solution may include a variety of additional property modifiers, as long as these property modifiers do not interfere with the function of the indicator dye or dye mixture. Examples of property modifiers that can be used include, for example, wetting agents, UV stabilizers, antistatic agents, gel-forming agents, colorants, slip modifiers, thixotropic agents, tack promoting agents, tack reducing agents, foaming agents, antifoaming agents, flow or other rheology control agents, waxes, oils, plasticizers, binders, antioxidants, fungicides, bactericides, organic and/or inorganic filler particles, leveling agents, opacifiers, dispersants, and the like.

The dye solution can be coated in a variety of ways using a variety of different types of equipment. For example, when carried out on a small scale, such as in a laboratory, the coating may be carried out using a micropipette. For larger scale coating, coaters such as spray coaters, gravure coaters, curtain coaters, fluid bearing die coaters or printers such as, for example, inkjet printers can be used. After coating, the coated inert, porous substrate may be dried to remove the solvent. This drying can be done at room temperature or at elevated temperature by using, for example, an oven, such as a forced air oven.

To the inert, porous substrate with the indicator dye coated on it, is laminated a layer of inert adhesive. As described above, this adhesive layer may be in the form of a transfer tape or a tape with a backing. If a transfer tape is used, additional layers may be laminated to the exposed adhesive surface, or the exposed adhesive surface may be covered with a release liner which can be removed to attach the chemical indicator to a surface. It may be desirable to laminate these additional layers one layer at a time or it may be desirable to prepare a multilayer adhesive construction and laminate this construction to the inert, porous substrate with the indicator dye coated on it. This multilayer adhesive construction can include multiple adhesive layers, and/or film layers as long as there is an inert adhesive layer capable of being laminated to the inert, porous substrate.

The present disclosure includes the following embodiments.

Among the embodiments are chemical indicators. A first embodiment includes a chemical indicator comprising: an inert, porous substrate; an indicator dye or mixture of dyes contained within at least some of the pores of the inert, porous substrate; and an inert adhesive layer attached to the inert, porous substrate.

Embodiment 2 is the chemical indicator of embodiment 1, wherein the inert, porous substrate comprises a microporous substrate, wherein substantially all of the pores are less than 1,000 micrometers in diameter.

Embodiment 3 is the chemical indicator of embodiment 2, wherein substantially all of the pores are from 1-500 micrometers in diameter.

Embodiment 4 is the chemical indicator of embodiment 2, wherein substantially all of the pores are from 1-100 micrometers in diameter.

Embodiment 5 is the chemical indicator of embodiment 2, wherein substantially all of the pores are from 1-10 micrometers in diameter.

Embodiment 6 is the chemical indicator of any of embodiments 1-5, wherein the porous substrate comprises a polymeric porous substrate.

Embodiment 7 is the chemical indicator of embodiment 6, wherein the polymeric porous substrate comprises polyethylene, polypropylene or other hydrocarbon polymer or mixture thereof.

Embodiment 8 is the chemical indicator of any of embodiments 1-7, wherein the inert, porous substrate comprises a membrane prepared by thermally induced phase separation.

Embodiment 9 is the chemical indicator of embodiment 8, wherein the membrane comprises polypropylene.

Embodiment 10 is the chemical indicator of any of embodiments 1-9, wherein the indicator dye comprises an acid indicator dye, or a base indicator dye.

Embodiment 11 is the chemical indicator of any of embodiments 1-10, wherein the inert adhesive layer comprises an adhesive layer substantially free of acid-containing and base-containing units.

Embodiment 12 is the chemical indicator of any of embodiments 1-11, wherein the inert adhesive layer comprises a natural rubber adhesive, a synthetic rubber adhesive, a poly-alpha-olefin adhesive, a styrene block copolymer adhesive, a poly-(meth)acrylate adhesive, a silicone adhesive or mixtures thereof.

Embodiment 13 is the chemical indicator of any of embodiments 1-12, further comprising a non-porous layer attached to the inert porous substrate by an adhesive layer.

Embodiment 14 is the chemical indicator of embodiment 13, wherein the non-porous layer comprises a film or tape backing.

Embodiment 15 is the chemical indicator of any of embodiments 13-14, further comprising a second adhesive layer adjacent to the non-porous layer.

Embodiment 16 is the chemical indicator of embodiment 15, wherein the second adhesive layer comprises the same adhesive as the inert adhesive layer.

Embodiment 17 is the chemical indicator of embodiments 15, wherein the second adhesive layer comprises an adhesive different from the inert adhesive layer.

Embodiment 18 is the chemical indicator of any of embodiments 15-17, wherein the second adhesive layer comprises and optically clear adhesive layer.

Embodiment 19 is the chemical indicator of any of embodiments 15-18, further comprising a release liner attached to the second adhesive layer.

Among the embodiments of this disclosure are devices. Embodiment 20 comprises a device comprising: a case; and at least one chemical indicator within the case, the chemical indicator comprising: an inert, porous substrate; and an indicator dye or mixture of dyes contained within at least some of the pores of the inert, porous substrate; and an inert adhesive layer attached to the inert, porous substrate.

Embodiment 21 is the device of embodiment 20, wherein the adhesive layer attaches the chemical indicator to the surface of the case.

Embodiment 22 is the device of any of embodiments 20-21, wherein the inert, porous substrate comprises a microporous substrate, wherein substantially all of the pores are less than 1,000 micrometers in diameter.

Embodiment 23 is the device of embodiment 22, wherein substantially all of the pores are from 1-500 micrometers in diameter.

Embodiment 24 is the device of embodiment 22, wherein substantially all of the pores are from 1-100 micrometers in diameter.

Embodiment 25 is the device of embodiment 22, wherein substantially all of the pores are from 1-10 micrometers in diameter.

Embodiment 26 is the device of any of embodiments 20-25, wherein the indicator dye comprises an acid indicator dye or a base indicator dye.

Embodiment 27 is the device of any of embodiments 20-26, further comprising additional chemical indicators, wherein the additional chemical indicators may be the same or different from the at least one chemical indicator.

Embodiment 28 is the device of any of embodiments 20-27, wherein the case comprises a respirator cartridge.

Embodiment 29 is the device of any of embodiments 20-28, wherein the inert adhesive layer comprises a transparent adhesive layer.

Embodiment 30 is the device of any of embodiments 20-29, further comprising a non-porous layer attached to the inert porous substrate by the inert adhesive layer.

Embodiment 31 is the device of embodiment 30, further comprising a second adhesive layer attached to the non-porous layer.

Embodiment 32 is the device of any of embodiments 30-31, wherein the non-porous layer comprises a film or tape backing.

Embodiment 33 is the device of any of embodiments 30-32, wherein the non-porous layer comprises a transparent layer.

Embodiment 34 is the device of embodiment 31, wherein the second adhesive layer comprises the same adhesive as the inert adhesive layer.

Embodiment 35 is the device of embodiment 31, wherein the second adhesive layer comprises an adhesive different from the inert adhesive layer.

Embodiment 36 is the device of any of embodiments 31 or 34-35, wherein the second adhesive layer comprises and optically clear adhesive layer.

Embodiment 37 is the device of any of embodiments 31 or 34-36, further comprising a release liner attached to the second adhesive layer.

Among the embodiments of this disclosure are methods of preparing chemical indicators. Embodiment 38 includes the method of preparing a chemical indicator comprising: providing an inert, porous substrate; providing an indicator dye solution; applying the indicator dye solution to the inert, porous substrate such that at least some of the indicator dye mixture enters the pores of the inert, porous substrate; and applying a layer of inert adhesive to the porous substrate.

Embodiment 39 is the method of embodiment 38, wherein applying a layer of inert adhesive to the porous substrate comprises laminating an inert adhesive layer to the porous substrate.

Embodiment 40 is the method of any of embodiments 38-39, further comprising drying the inert, porous substrate after applying the indicator dye solution.

EXAMPLES

These examples are merely for illustrative purposes only and are not meant to be limiting on the scope of the appended claims. All parts, percentages, ratios, etc. in the examples and the rest of the specification are by weight, unless noted otherwise. Solvents and other reagents used were obtained from Sigma-Aldrich Chemical Company; Milwaukee, Wis. unless otherwise noted.

Table of Abbreviations

| Abbreviation or Trade Designation | Description |
| --- | --- |
| TIPS | Porous polypropylene membrane made according to the teachings of U.S. Pat. Nos. 5,120,594 and 5,238,623. |
| Dye-1 | Methyl Red, (CAS# 76-59-5). |
| Adhesive-1 | Transfer tape prepared as described in U.S. Pat. No. 5,859,088, Example 1. |
| Adhesive-2 | Transfer Tape of 3M OPTICALLY CLEAR ADHESIVE 8172, commercially available form 3M Company, St. Paul, MN. |
| Tape-1 | Tape of 3M SCOTCH MAGIC TAPE 810, commercially available from 3M Company, St. Paul, MN. |
| Respirator Cartridge | A 3M Organic Vapor Cartridge 6001 from 3M Company, St. Paul, MN, filled with of 46.0 g of GG carbon. |
| GG carbon | Commercially available from Kuraray Chemical Company, Osaka, Japan. |

Synthesis Examples

Synthesis Example S1

Preparation of Dye Solution

A solution of Dye-1 was prepared in ethanol solution using the reagents listed in Table S1. The solid dye was placed in a glass vial, ethanol was added to dissolve the dye, and 1.0 N NaOH (aq) was added to basify the solution.

TABLE S1

| Dye | Dye amount (mg) | EtOH amount (µL) | 1.0N NaOH (aq) amount (µL) |
| --- | --- | --- | --- |
| Dye-1 | 3.4 | 945 | 57 |

Example 1

A sample of TIPS membrane was coated with the Dye-1 solution prepared in the Synthesis Example S1. The dye solution was deposited onto the membrane using a micropipet to place 2.0 microliters of dye solution on the membrane. The sample was then dried in air in the dark for several hours. sensor devices were prepared by laminating the coated TIPS membrane to an adhesive or a tape as described in Table 1 below. The adhesive laminated sensor device was attached to a sample Respirator Cartridge. The Respirator Cartridge with sensor device attached was exposed to an $SO_2$ flow of 32 liters per minute (Lpm) at 43% relative humidity (RH) and 9.2 ppm of $SO_2$ gas with the concentration of $SO_2$ at the outlet side monitored for breakthrough. The sensor devices were monitored using an Olympus C-5060 CAMEDIA camera with aperture 3.2, shutter speed 1/8, close focus, and delayed flash. The results of the camera and outlet monitor are summarized in Table 2 below.

TABLE 1

| Example | Adhesive Layer |
|---|---|
| 1A | Adhesive-1 |
| 1B | Adhesive-2 |
| 1C | Tape-1 |

TABLE 2

| Elapsed Time (Hr:Min) | Example 1A | Example 1B | Example 1C | Outlet Monitor (ppm $SO_2$) |
|---|---|---|---|---|
| 0:00 | Yellow | Yellow | Yellow | 0.0 |
| 2:15 | Yellow | Yellow | Yellow | 0.0 |
| 4:00 | Yellow | Yellow | Yellow | 0.0 |
| 6:20 | Yellow | Yellow | Yellow | 0.0 |
| 21:45 | Red | Red | Red | 0.1 |

Example 2

A sample of TIPS membrane was coated with the Dye-1 solution prepared in the Synthesis Example S1. The dye solution was deposited onto the membrane using a micropipet to place 2.0 microliters of dye solution on the membrane. The sample was then dried in air in the dark for several hours. Sensor devices were prepared by laminating the coated TIPS membrane to an adhesive or a tape as described in Table 3 below. The adhesive laminated sensor device was attached to a sample Respirator Cartridge. The Respirator Cartridge with sensor device attached was exposed to an $SO_2$ flow of 32 liters per minute (Lpm) at 43% relative humidity (RH) and 8.3 ppm of $SO_2$ gas with the concentration of $SO_2$ at the outlet side of the Respirator Cartridge monitored for breakthrough. The sensor devices were monitored using an Olympus C-5060 CAMEDIA camera with aperture 3.2, shutter speed 1/8, close focus, and delayed flash. The results of the camera and outlet monitor are summarized in Table 4 below.

TABLE 3

| Example | Adhesive Layer |
|---|---|
| 2A | Adhesive-1 |
| 2B | Adhesive-2 |
| 2C | Tape-1 |

TABLE 4

| Elapsed Time (Hr:Min) | Example 2A | Example 2B | Example 2C | Outlet Monitor (ppm $SO_2$) |
|---|---|---|---|---|
| 0:00 | Yellow | Yellow | Yellow | 0.0 |
| 4:05 | Yellow | Yellow | Yellow | 0.0 |
| 6:00 | Yellow | Yellow | Yellow | 0.0 |
| 8:00 | Yellow | Yellow | Yellow | 0.0 |
| 23:45 | Red | Red | Red | 0.0 |
| 25:40 | Red | Red | Red | 0.1 |

What is claimed is:

1. A chemical indicator comprising:
an inert, porous substrate;
an indicator dye or mixture of dyes contained within at least some of the pores of the inert, porous substrate, wherein the indicator dye or mixture of dyes is coated on the inert, porous substrate dissolved in a solvent and dried to remove the solvent, wherein the solvent consists of methanol, ethanol, isopropanol, acetone, methyl ethyl ketone, ethyl acetate, ethyl ether, tetrahydrofuran, or dichloromethane; and
an inert pressure sensitive adhesive layer attached to the inert, porous substrate.

2. The chemical indicator of claim 1, wherein the inert, porous substrate comprises a microporous substrate, wherein substantially all of the pores are less than 1,000 micrometers in diameter.

3. The chemical indicator of claim 1, wherein the inert, porous substrate comprises a polymeric porous substrate.

4. The chemical indicator of claim 3, wherein the polymeric porous substrate comprises polyethylene, polypropylene or other hydrocarbon polymer or mixture thereof.

5. The chemical indicator of claim 1, wherein the inert, porous substrate comprises a membrane prepared by thermally induced phase separation.

6. The chemical indicator of claim 1, wherein the indicator dye comprises an acid indicator dye, or a base indicator dye.

7. The chemical indicator of claim 1, wherein the inert pressure sensitive adhesive layer comprises an adhesive layer substantially free of acid-containing and base-containing units.

8. The chemical indicator of claim 1, wherein the inert pressure sensitive adhesive layer comprises a natural rubber adhesive, a synthetic rubber adhesive, a poly-alpha-olefin adhesive, a styrene block copolymer adhesive, a poly-(meth)acrylate adhesive, a silicone adhesive or mixtures thereof.

9. The chemical indicator of claim 1, further comprising a non-porous layer attached to the inert porous substrate by an adhesive layer.

10. A device comprising:
a case; and
at least one chemical indicator within the case, the chemical indicator comprising:
an inert, porous substrate; and
an indicator dye or mixture of dyes contained within at least some of the pores of the inert, porous substrate, wherein the indicator dye or mixture of dyes is coated on the inert, porous substrate dissolved in a solvent and dried to remove the solvent, wherein the solvent consists of methanol, ethanol, isopropanol, acetone, methyl ethyl ketone, ethyl acetate, ethyl ether, tetrahydrofuran, or dichloromethane; and an inert pressure sensitive adhesive layer attached to the inert, porous substrate.

11. The device of claim 10, wherein the pressure sensitive adhesive layer attaches the chemical indicator to the surface of the case.

12. The device of claim 10, wherein the inert, porous substrate comprises a microporous substrate, wherein substantially all of the pores are less than 1,000 micrometers in diameter.

13. The device of claim 10, wherein the indicator dye comprises an acid indicator dye or a base indicator dye.

14. The device of claim 10, further comprising additional chemical indicators, wherein the additional chemical indicators may be the same or different from the at least one chemical indicator.

15. The device of claim 10, wherein the case comprises a respirator cartridge.

16. The device of claim 10, further comprising a non-porous layer attached to the inert porous substrate by the inert pressure sensitive adhesive layer.

17. The device of claim 16, further comprising a second adhesive layer attached to the non-porous layer.

18. The device of claim 10, wherein the inert pressure sensitive adhesive layer comprises a transparent pressure sensitive adhesive layer.

19. A method of preparing a chemical indicator comprising:
- providing an inert, porous substrate;
- providing an indicator dye solution;
- applying the indicator dye solution to the inert, porous substrate such that at least some of the indicator dye mixture enters the pores of the inert, porous substrate;
- drying the inert, porous substrate to remove the solvent, wherein the solvent consists of methanol, ethanol, isopropanol, acetone, methyl ethyl ketone, ethyl acetate, ethyl ether, tetrahydrofuran, or dichloromethane; and
- applying a layer of inert pressure sensitive adhesive to the porous substrate.

20. The method of claim 19, wherein applying a layer of inert pressure sensitive adhesive to the porous substrate comprises laminating an inert pressure sensitive adhesive layer to the porous substrate.

\* \* \* \* \*